United States Patent [19]

Fjare et al.

[11] Patent Number: 4,855,503

[45] Date of Patent: Aug. 8, 1989

[54] PREPARATION OF P,P'-OXYBIS(ANILINE)

[75] Inventors: Douglas E. Fjare, Naperville; Gary P. Hagen, Glen Ellyn, both of Ill.

[73] Assignee: Amoco Corporation, Chicago, Ill.

[21] Appl. No.: 41,480

[22] Filed: Apr. 23, 1987

[51] Int. Cl.$^4$ .............................................. C07C 85/147
[52] U.S. Cl. .................... 564/394; 564/393; 564/430
[58] Field of Search ................. 564/393, 394, 430

[56] References Cited

U.S. PATENT DOCUMENTS

| | | | |
|---|---|---|---|
| 3,140,316 | 7/1964 | Towle | 260/580 |
| 3,175,007 | 3/1965 | Berhenke | 260/571 |
| 3,914,310 | 10/1975 | Frick et al. | 260/571 |
| 4,539,428 | 9/1985 | Merrell et al. | 564/430 |
| 4,551,551 | 11/1985 | Inskip | 564/430 |

FOREIGN PATENT DOCUMENTS

| | | | |
|---|---|---|---|
| 1909520 | 9/1970 | Fed. Rep. of Germany | 564/430 |
| 307798 | 7/1930 | United Kingdom | 564/394 |

OTHER PUBLICATIONS

Snyder, H. R. *Journal of the American Chemical Soc.* (1953), vol. 75, pp. 2014–2015.

*Primary Examiner*—Richard L. Raymond
*Assistant Examiner*—Peter G. O'Sullivan
*Attorney, Agent, or Firm*—Gunar J. Blumberg; William H. Magidson; Ralph C. Medhurst

[57] ABSTRACT

Oxybisaniline is prepared in high yield by reacting a hydroxylamine with a polycarboxylic diphenyl ether in the presence of an inorganic acid. The acid groups are directly converted to amine groups. By-products of the reaction are negligible.

8 Claims, No Drawings

PREPARATION OF P,P'-OXYBIS(ANILINE)

FIELD OF THE INVENTION

This invention relates to a method for the preparation of p,p'-oxybis(aniline), also named 4,4'-diaminodiphenyl ether, from hydroxylamine and 4,4'-dicarboxydiphenyl ether in high yield. More particularly, it relates to the preparation of p,p'-oxybis(aniline), hereafter called "oxybisaniline," by direct conversion of an acid group to an amine group, wherein the Lossen Rearrangement is applied to a polyacid compound wherein a polyacid compound is reacted with a hydroxylamine and polyphosphoric acid, and the product is hydrolyzed at a rate of hydrolysis which maximizes yield of p,p'-oxybisaniline.

BACKGROUND OF THE INVENTION

Oxybisaniline (OBA) is an important monomer for preparation of polyamide-imides and polyimides. Polytrimellitimides, for example, are prepared by the reaction between an acid halide of a benzene tricarboxylic acid anhydride and an organic diamine such as oxybisaniline. Polytrimellitimides are useful as polymeric wire enamels which exhibit many desirable properties. Polyimides are useful in film and shaped articles for high performance applications.

Oxybisaniline can be prepared in a number of ways, two of the more common methods being the reduction of bis(p-nitrophenyl) ether and the ammonolysis of the corresponding dichloro or dibromo diphenyl ether. In such preparation, because of impurities in the starting material or side reactions which occur during the process, there are produced various undesirable by-products including both monofunctional and difunctional compounds such as phenoxyaniline, halo or nitrophenoxyaniline, aminophenoxyphenol, and the like. Position isomers of oxybisaniline may also be present in the product. The preparation of pure oxybisaniline is also often complicated by the presence in the crude product of highly colored contaminants such as iron compounds or materials formed by decomposition or oxidation of amino groups.

Methods are known whereby such colored impurities can be removed from a product. For example, most or all of the tarry decomposition products can be separated by treating a solution of the impure product with activated carbon. Iron compounds are advantageously reduced to the ferrous state and thereby maintained in solution while the oxybisaniline is precipitated or crystallized and separated by filtration. Such reduction also is effected by reducing some of the colored organic impurities. Compounds such as sodium dithionite, sodium bisulfite, and sodium formaldehyde sulfoxylate are effective reducing agents for this purpose.

It is also known that some by-products, particularly compounds of lower functionality than the desired product, are effectively removed by extracting an aqueous solution of a strong mineral acid salt of oxybisaniline with a water-immiscible solvent such as an aliphatic ketone of five to eight carbon atoms, a polychlorinated lower aliphatic hydrocarbon, or an aromatic hydrocarbon of the benzene series. This extraction procedure is also effective to some extent in removing difunctional impurities from the product. However, complete removal of these materials from oxybisaniline is not possible by this method.

It has now been found that oxybisaniline can be prepared in high yield and a highly purified grade of product can be obtained by reaction of a hydroxylamine and 4,4'-dicarboxydiphenyl ether by means of a Lossen Rearrangement. This reaction is accomplished by reacting the hydroxylamine with 4,4'-dicarboxydiphenyl ether in polyphosphoric acid after a minimum temperature of 140° C. has been reached. At a reaction temperature of less than 140° C., the reaction rate is very slow and conversion of the starting materials to oxybisaniline is not complete. Hydrolysis of the reaction mixture yields oxybisaniline in high yield. Production of by-products as has been the common result in other methods of preparing oxybisaniline is negligible.

The Lossen Rearrangement to convert aromatic acids and their derivatives to amines has been described by Snyder, et al., JACS, 75, 2014 (1953). The reaction, according to Snyder, is carried out by heating a mixture of the reactants, comprising aromatic acids, hydroxylamine and polyphosphoric acid, with stirring, until rapid evolution of carbon dioxide begins, usually in the range of 150° C. to 170° C. At such temperatures, the reaction normally is complete in five to ten minutes, and the mixture is poured over crushed ice to give an aqueous solution of the amine phosphate. The yields of the crude products, as reported by Snyder, ranged from zero to as high as 82%. Snyder explained the range of yields in that acids containing electron-donating substituents were found to give higher yields than those containing electron-withdrawing groups. Melting points of the products indicated the crude products required further purification. Synder reported that acids which gave poor yields of amines produced large amounts of dark-colored acid-insoluble material of very indefinite melting point. Snyder reported that valeric and caprylic acids failed to yield more than mere traces of the expected amines. Caprylohydroxamic acid also failed to yield an amine.

SUMMARY OF THE INVENTION

A process is disclosed for preparation of 4,4'-oxybisaniline in high yield. By-product production of the process is negligible. Reaction is between a hydroxylamine and a polycarboxylicdiphenyl ether in the presence of polyphosphoric acid, followed by hydrolysis to a pH between 6 and 8.

DETAILS OF THE INVENTION

Unexpectedly, it has now been found that the Lossen Rearrangement can be applied to aromatic polyacids despite the presence of the electron-withdrawing substituents, i.e., the two carboxylic acid groups.

It has now been found that hydrolysis of the Lossen Rearrangement reaction products within a pH range of 6 to 8 provides a precipitated amine product in improved yield and higher purity than is taught in prior procedures.

Bases suitable for the precipitation step are those capable of liberating the free amine from its acid salt. These bases include ammonium hydroxide, alkali metal hydroxides and carbonates, and alkaline earth metal hydroxides. An alcoholic solution of an alkali metal hydroxide such as sodium or potassium hydroxide can be the base. While addition of sufficient base to the salt solution to obtain a mixture having a pH in excess of 5 will yield good results, the purification process is most efficient when the neutralization, which comprises the hydrolysis of the polyphosphoric acid, is continued to a final pH in excess of about 6 and less than 8.

The precipitation can be carried out at any temperature where the reaction medium is liquid, i.e., between its freezing and boiling points. Preferably, the base is added to the acidic salt solution at about 50°–80° C. and the neutralized slurry is then cooled below about 30° C. to obtain as complete a separation as possible of solid p,p′-oxybisaniline from the aqueous alkanol.

An aqueous alkanol solution can be used in place of water to improve product purity. However, a yield loss can occur. The alcohol can be an aliphatic alcohol of one to eight carbon atoms miscible in water in all proportions.

The proportion of aqueous alkanol to oxybisaniline salt is not a critical factor in the process so long as there is initially present sufficient water to dissolve the salt completely. Where higher concentrations of alcohol are employed, it is particularly desirable to hold the total volume of solvent to a minimum to ensure precipitation rather than solution of the liberated amine upon addition of base and also to obtain good product recovery.

The process can be operated in a number of ways within the general description above. For example, the impure oxybisaniline can be dissolved in aqueous mineral acid and then precipitated by addition of an aqueous base solution. Alternatively, the oxybisaniline salt may be dissolved in aqueous alkanol and precipitated by addition of aqueous base. A feature of the invention is the precipitation of the free amine from its acid salt in the aqueous or aqueous alkanol medium.

Since the primary effect of the present process is to remove difunctional impurities from oxybisaniline while the main effect of the extraction process previously mentioned is to remove impurities of lower functionality, although both procedures reduce to some extent the quantities of other impurities present, best results are obtained and it is preferred to operate by using a combination of the two purification process, e.g. forming a water solution of a strong mineral acid salt of the crude oxybisaniline, extracting that solution with a suitable water-immiscible solvent, and subjecting the extracted solution to the present precipitation process.

Suitable solvents for use as extractants include aliphatic ketones of 5–8 carbon atoms such as methyl propyl ketone, methyl isobutyl ketone, diethyl ketone, and methyl hexyl ketone, chlorinated lower aliphatic hydrocarbons such as chloroform, methylchloroform, ethylene dichloride, tetrachloroethylene, trichloropropene, and the like, and aromatic hydrocarbons such as benzene, toluene, xylene, ethylbenzene, mesitylene, and similar compounds. Chloroform and methyl isobutyl ketone are particularly preferred extracting solvents.

The extraction is carried out using an acidic aqueous solution of a strong mineral acid salt of oxybisaniline at a pH of about 2.5 to 3.5. Such a solution is conveniently obtained by dissolving a mole of oxybisaniline in an aqueous solution containing about 1.9 equivalents of a strong mineral acid in such dilution that the final salt solution contains about 10%–25% by weight of the dissolved solids. The hydrochloride of oxybisaniline is the preferred acid salt. The extraction can be run at any temperature where the salt solution remains liquid and homogenous. It is preferably run at ambient temperature and atmospheric pressure. Higher pressures can be used but are not required.

Accordingly, the instant invention comprises a synthesis of oxybisaniline which utilizes starting materials significantly different than those used in present commercial processes. Oxybisaniline has been prepared in high yield by reacting 4,4′-dicarboxydiphenyl ether with a hydroxylamine in polyphosphoric acid. $NH_2OH \cdot HCl$ or $(NH_2OH)_3 \cdot H_3PO_4$ is the preferred hydroxylamine. $NH_2OH \cdot HCl$ is the more preferred hydroxylamine because of availability. The reaction occurs readily after a minimum temperature of 140° has been reached. Polyphosphoric acid is used as the solvent because of its excellent properties as a nonoxidizing dehydrating reagent. The net reaction is written below:

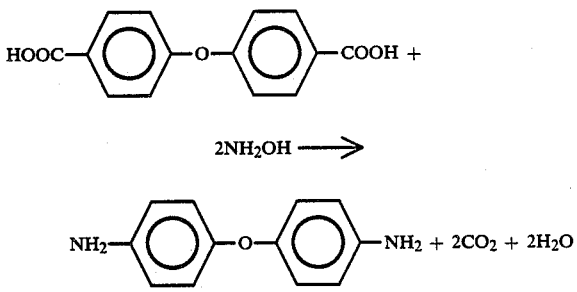

This reaction also can be performed starting with any diester of 4,4′-dicarboxydiphenyl ether.

It is desirable to modify the polyphosphoric acid solvent so that polyphosphoric acid is not used in excess. Guette, et. al., have reported using polyphosphoric acid in the presence of a cosolvent where the amount of polyphosphoric acid required has been decreased by a factor of five (*Synthesis* 1980, 222). Palomo and Ganboa have described the use of polyphosphoric acid in acetic acid (*Synth. Comm.* 1983, 13, 999). These articles suggest that it is not always necessary to use a large excess of polyphosphoric acid. A useful extension of this idea would be to use a stoichiometric amount of polyphosphoric acid in a molten salt solvent. The salts which will probably work best in this capacity are the tetraalkyl ammonium (or phosphonium) tetrafluoroborates (or hexafluorophosphates). A requirement is that the anion be nonoxidizable under the reaction conditions, hence, tetrabutylphosphonium bromide is not a suitable solvent.

Other dehydrating agents besides polyphosphoric acid can be used to convert hydroxamic acids into amines. Those are acetic anhydride, phosphorous pentoxide, carbodiimides, and sulfur trioxide. Thus, an alternative to polyphosphoric acid can be oleum (sulfur trioxide in sulfuric acid).

Accordingly, the instant invention comprises a process for preparation of p,p′-oxybisaniline in high yield and in highly pure state which comprises the combination of the steps of (a) reacting a solution of a mixture comprising a polyacid consisting essentially of 4,4′-dicarboxydiphenyl ether and a hydroxylamine salt of an inorganic acid, in the presence of polyphosphoric acid at a temperature within the range of from about 150° C. to about 180° C.; (b) chilling said reaction mixture to a temperature of from about 0° C. to about +100° C.; (c) neutralizing said reaction mixture with an aqueous solution of a base to a pH of from 6 to 8; (d) reacidifying said reaction mixture with an aqueous mineral acid to a pH of less than 5 and at a temperature within the range of from about 0° C. to about 100° C.; (e) separating acid-insoluble impurities from said mixture to recover the mother liquor; (f) neutralizing said mother liquor with an aqueous solution of a base to a pH within the range of from 5 to 14 to precipitate p,p'-oxybisaniline and (g) separating said mother liquor and precipitate to recover p,p'-oxybisaniline. The hydroxylamine salt of an inorganic acid can be selected from the group consisting of $NH_2OH \cdot HCl$ and $(NH_2OH)_3 \cdot H_3PO_4$. The said base can be selected from the group consisting of ammonium hydroxide, an alkali metal hydroxide, an alkali metal carbonate, and an alkaline earth metal hydroxide. The said alkali metal hydroxide can be selected from the group consisting of potassium hydroxide, sodium hydroxide, calcium hydroxide, lithium hydroxide, barium hydroxide, magnesium hydroxide, calcium hydroxide and rubidium hydroxide. The said mineral acid can be selected from the group consisting of sulfuric acid, hydrochloric acid, and phosphoric acid. The said aqueous solution can comprise a solution of a base, water and an aliphatic alkanol of one to eight carbon atoms. Preferably, the said alkali metal hydroxide is sodium hydroxide and said mineral acid is phosphoric acid. Separation can be by filtration, or by any other suitable means, as by centrifuge.

The invention is further illustrated but is not intended to be limited by the following examples.

The preparation of oxybisaniline without the practice of the instant invention is set forth in Example I to better educate the field of the application of the invention to the workers in the art.

EXAMPLE I

Oxybisbenzoic acid (OBBA) (0.97 g, 3.76 mmole) and hydroxylamine hydrochloride (0.59 g, 8.5 mmole) were placed in a 3-neck round bottom flask with 10.5 g of polyphosphoric acid. The flask was stirred mechanically and heated to 160° C. After 15 min. at 160° C., the contents of the flask were poured into 50 g of crushed ice, then filtered. The filtrate was basified with enough 20% KOH to bring it to pH 7. This solution was then filtered to give 0.40 g of tan crystals, m.p.=183°–185° C., 53% yield based on OBBA. The product was identified as oxybisaniline by comparison with an authentic sample. The melting point of 99+% pure OBA is 190°–192° C.

EXAMPLE II

OBBA (1.20 g, 4.62 mmole) and hydroxylamine hydrochloride (0.77 g, 11.1 mmole) were placed in a round bottom flask with 11.3 g of polyphosphoric acid. The flask was filled with nitrogen and kept under a slow stream of nitrogen. After 10 min at 160° C., the contents of the flask were poured into 50 g of crushed ice and basified with 20% KOH to pH 7. After stirring for 2 hours at room temperature, enough concentrated phosphoric acid was added so that the pH was less than 5. This solution was filtered, then basified again with 20% KOH to precipitate 0.83 g of crystalline oxybisaniline, 89% yield, based on OBBA.

EXAMPLE III

OBBA (1.20 g, 4.62 mmole) and hydroxylamine hydrochloride (0.77 g, 9.23 mmole) were placed in a round bottom flask with 10.1 g of polyphosphoric acid and slowly heated to 170° C. The contents of the flask were kept under a slow stream of nitrogen. After reaching 170° C., the reaction mixture was poured into crushed ice and then filtered. Enough 20% potassium hydroxide solution was added to the filtrate to bring the pH to 7. The crystalline oxybisaniline was filtered and after drying weighed 0.46 g (50% yield).

This example shows that high yield obtained in Example II was not due to running the reaction under an inert atmosphere. The high yield of Example II was due to the neutral hydrolysis of polyphosphoric acid, prior to isolation of crystalline oxybisaniline.

EXAMPLE IV

The procedure of Example II was repeated, using OBBA (1.50 g, 5.81 mmole), hydroxylammonium phosphate (0.84 g, 4.26 mmole) and 15 g of polyphosphoric acid. Oxybisaniline was isolated in 87% yield, based on OBBA, M.P. 190°–192° C. Hydroxylammonium phosphate accordingly is an acceptable form of a hydroxylamine for this reaction.

EXAMPLE V

The procedure of Example III was repeated, using OBBA (1.00 g, 3.85 mmole), hydroxylammonium sulfate (0.77 g, 4.62 mmole) and 12.2 g of polyphosphoric acid. Oxybisaniline was isolated in 29% yield. Hydroxylammonium sulfate accordingly is not considered to be a suitable hydroxylamine because of the low yield obtained of product.

EXAMPLE VI

The procedure of Example III was repeated, using OBBA (1.00 g, 3.85 mmole), hydroxylamine-0-sulfonic acid (1.08 g, 9.3 mmole), and 10.3 g of polyphosphoric acid. Oxybisaniline was isolated in 11% yield. Hydroxylamine-0-sulfonic acid accordingly is not considered to be a suitable hydroxylamine because of the low yield obtained of product.

What is claimed is:

1. A process for preparation of p,p'-oxybisaniline in high yield and in a highly pure state which comprises the combination of the steps of
   a. reacting a solution of a reaction mixture comprising a polyacid consisting essentially of 4,4'-dicarboxydiphenyl ether and a hydroxylamine salt of an inorganic acid, in the presence of polyphosphoric acid at a minimum temperature of about 140° C.;
   b. neutralizing said reaction mixture with an aqueous solution of a base to a pH of from 6 to 8 said neutralizing with an aqueous solution of base to a pH of from 6 to 8 being carried out for a period of time that is sufficient to hydrolyze said polyphosphoric acid;
   c. reacidifying said reaction mixture with an aqueous mineral acid to a pH of less than 5 and at a temperature within the range of from about 0° C. to about 100° C.;
   d. separating acid-insoluble impurities from said mixture to recover the mother liquor;
   e. neutralizing said mother liquid with an aqueous solution of a base to a pH within the range of from 5 to 14 to precipitate p,p'-oxybisaniline; and
   f. separating said mother liquor and precipitate to recover p,p'-oxybisaniline.

2. The process of claim 1 wherein hydroxylamine salt of an inorganic acid is selected from the group consisting of $NH_2OH \cdot HCl$ and $(NH_2OH)_3 \cdot H_3PO_4$.

3. The process of claim 1 wherein said base is selected from the group consisting of ammonium hydroxide, an alkali metal hydroxide, an alkali metal carbonate, and an alkaline earth metal hydroxide.

4. The process of claim 3 wherein said alkali metal hydroxide is selected from the group consisting of potassium hydroxide, sodium hydroxide, calcium hydroxide, lithium hydroxide, barium hydroxide, magnesium hydroxide, calcium hydroxide and rubidium hydroxide.

5. The process of claim 3 wherein said alkali metal hydroxide is sodium hydroxide.

6. The process of claim 1 wherein said mineral acid is selected from the group consisting of sulfuric acid, hydrochloric acid, and phosphoric acid.

7. The process of claim 6 wherein said mineral acid is phosphoric acid.

8. The process of claim 1 wherein said aqueous solution comprises a solution of a base, water and an aliphatic alkanol of one to eight carbon atoms.

* * * * *

UNITED STATES PATENT OFFICE
CERTIFICATE OF CORRECTION

Patent No. 4,855,503                    Dated August 8, 1989

Inventor(s) Douglas E. Fjare & Gary P. Hagen

It is certified that error appears in the above-identified patent and that said Letters Patent is hereby corrected as shown below:

| Col. | Line | | |
|---|---|---|---|
| 2 | 19-20 | "hydroxy-lamine" should read --hydroxyl-amine-- | |
| 4 | 5 | "$NH_2OH.HCl$" should read --$NH_2OH \cdot HCl$-- | |
| 4 | 5 | "$(NH_2OH)_3 \cdot H_3PO_4$" should read --$(NH_2OH)_3 \cdot H_3PO_4$-- | |
| 4 | 6 | "$NH_2OH.HCl$" should read --$NH_2OH \cdot HCl$-- | |
| 5 | 7 | "$NH_2OH.HCl$" should read --$NH_2OH \cdot HCl$-- | |
| 5 | 7 | "$(NH_2OH)_3 \cdot H_3PO_4$ should read --$(NH_2OH)_3 \cdot H_3PO_4$ | |
| 6 | 15-16 | "hydroxy-lamine" should read --hydroxyl-amine-- | |
| 6 | 64 | "$NH_2OH.HCl$" should read --$NH_2OH \cdot HCl$ | |
| 6 | 64 | "$(NH_2OH)_3 \cdot H_3PO_4$" should read --$(NH_2OH)_3 \cdot H_3PO_4$ | |

Signed and Sealed this

Twenty-fourth Day of July, 1990

*Attest:*

HARRY F. MANBECK, JR.

*Attesting Officer*      *Commissioner of Patents and Trademarks*